(12) United States Patent
Sundaram

(10) Patent No.: US 8,815,080 B2
(45) Date of Patent: Aug. 26, 2014

(54) ADIABATIC REACTOR TO PRODUCE OLEFINS

(75) Inventor: Kandasamy Meenakshi Sundaram, Old Bridge, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 12/359,931

(22) Filed: Jan. 26, 2009

(65) Prior Publication Data
US 2010/0191031 A1    Jul. 29, 2010

(51) Int. Cl.
   C10G 51/02    (2006.01)
   C07C 2/78     (2006.01)
   B01J 19/00    (2006.01)

(52) U.S. Cl.
   CPC .......... *C07C 2/78* (2013.01); *C10G 2300/1025* (2013.01); *C10G 2400/20* (2013.01); *C10G 2300/807* (2013.01); *B01J 19/0026* (2013.01)
   USPC ............. 208/75; 208/67; 208/72; 208/132; 585/648; 585/650; 585/652

(58) Field of Classification Search
   USPC ........ 585/648, 650, 652; 208/130, 67, 72, 75, 208/132
   See application file for complete search history.

(56) References Cited

U.S. PATENT DOCUMENTS

| | | | |
|---|---|---|---|
| 2,985,698 A * | 5/1961 | Pechtold et al. ............. | 585/324 |
| 3,365,387 A * | 1/1968 | Cahn et al. .................. | 208/106 |
| 3,557,241 A * | 1/1971 | Kivlen et al. ................ | 585/648 |
| 4,264,435 A * | 4/1981 | Read et al. .................. | 208/129 |
| 4,542,252 A | 9/1985 | Graziani et al. | |
| 4,617,109 A | 10/1986 | Wells et al. | |
| 5,147,511 A | 9/1992 | Woebcke | |
| 5,271,827 A * | 12/1993 | Woebcke ..................... | 208/132 |
| 5,358,626 A | 10/1994 | Gandman et al. | |
| 5,817,226 A * | 10/1998 | Lenglet ........................ | 208/130 |
| 5,976,352 A * | 11/1999 | Busson et al. ................ | 208/75 |
| 6,322,760 B1 * | 11/2001 | Busson et al. ............... | 422/198 |
| 7,164,053 B2 | 1/2007 | Binmore et al. | |
| 2003/0191020 A1 | 10/2003 | Bharadwaj et al. | |
| 2009/0270668 A1 | 10/2009 | Bailey et al. | |

FOREIGN PATENT DOCUMENTS

| | | | |
|---|---|---|---|
| GB | 560195 A | 3/1944 | |
| GB | 884634 A | 12/1961 | |
| WO | 84/01310 A1 | 4/1984 | |

OTHER PUBLICATIONS

DIPPR Project 801, Design Institute for Physical Properties, AIChE, on-line version available at www.knovel.com.*
Heynderickx, et al., "Optimization of the Decoking Procedure of an Ethane Cracker with a Steam/Air Mixture" in Ind. Eng. Chem. Res., 2006, 45, 7520-7529—month unknown.*

(Continued)

*Primary Examiner* — In Suk Bullock
*Assistant Examiner* — Bradley Etherton
(74) *Attorney, Agent, or Firm* — Osha • Liang LLP

(57) ABSTRACT

Processes for production of olefins from hydrocarbon feedstocks are provided. In one aspect, the processes of the present invention utilize coils passing through a pyrolysis furnace to partially convert a hydrocarbon feedstock to olefins, followed by further conversion of the hydrocarbon feedstock in an adiabatic reactor. A portion of the coils in the pyrolysis furnace carry the hydrocarbon feedstock and the remainder carry steam only. After a selected period of time, the material flowing through the coils is switched. By flowing steam through the coils that had previously contained the hydrocarbon feedstock, on-line decoking can occur. In another aspect, a high temperature reactor is used to convert methane or natural gas to olefins.

13 Claims, 6 Drawing Sheets

(56) References Cited

OTHER PUBLICATIONS

Hiller, et al., "Gas Production" in Ullmann's Encyclopedia of Industrial Chemistry, 2002, Wiley-VCH, pp. 1-4 and 12-15, available on-line Dec. 15, 2006.*
International Search Report and Written Opinion issued Aug. 30, 2010 in corresponding PCT application No. PCT/US2010/021628 (6 pages).
SRT Pyrolysis Furnace Module, Lummus Technology.
Office Action (w/translation) issued Nov. 7, 2012 in corresponding Korean application No. 10-2011-7016975 (7 pages).
Office Action issued Jun. 28, 2012 in corresponding Canadian application No. 2,748,051 (3 pages).
First Office Action (w/translation) issued Apr. 16, 2013 in corresponding Chinese application No. 201080006136.3 (23 pages).
Notification of Reasons for Rejection (w/translation) issued May 21, 2013 in corresponding Japanese application No. 2011-548098 (8 pages).
Office Action issued May 10, 2013 in corresponding Canadian application No. 2,798,536 (2 pages).
Extended European Search Report issued Apr. 11, 2014 in corresponding European application No. 10733844.4 (9 pages).
Decision on Rejection (with translation) issued Nov. 21, 2013 in corresponding Chinese application No. 201080006136.3 (18 pages).
Decision of Rejection (w/translation) issued Oct. 15, 2013 in corresponding Japanese application No. 2011-548098 (5 pages).

* cited by examiner

ADIABATIC REACTOR TO PRODUCE OLEFINS

FIELD OF THE INVENTION

The present invention relates to improved processes for production of olefins. In one aspect, the processes of the present invention utilize coils passing through a pyrolysis furnace to partially convert a hydrocarbon feedstock to olefins, followed by further conversion of the hydrocarbon feedstock in an adiabatic reactor. In another aspect, a high temperature reactor is used to convert methane or natural gas to olefins.

BACKGROUND

Olefins, such as ethylene and propylene, are valuable hydrocarbons that are used for production of products such as polyethylene and polypropylene. Olefins are typically produced by thermal cracking of a hydrocarbon feedstock. In a thermal cracking process, heavier hydrocarbons such as naptha undergo cracking at elevated temperatures to produce olefins containing from 2 to 4 carbon atoms.

Several processes exist for cracking heavier hydrocarbons to produce olefins. In one process that is commonly used, the feedstock to be converted is heated in a furnace by passing the feedstock through the furnace within a plurality of coils. The coils are arranged to enhance heat transfer from the interior of the furnace to the feedstock within the coil. The feedstock is heated and cracked, and the cracked effluent in the outlet from the coil is quenched to terminate the cracking reaction.

The cracking of hydrocarbons in this manner results in the formation of various by-products, including coke. Coke forms on the internal surfaces of the coil and inhibits heat transfer from the furnace to the hydrocarbon feedstock. The amount of coke formed in the coils is directly related to the conversion level of the hydrocarbon feedstock. Because radiant heat is supplied to the metal coils, coke deposition inhibits heat transfer and causes the temperature of the metal coils to rise, which can result in damage to the coils. At some point, the coke fouling inhibits heat transfer to the point that the coils must be taken off-line for decoking. Decoking is typically performed using steam and air to burn the coke off of the interior of the coils. Because the decoking process requires the equipment to be taken off-line, production of olefins from the reactor halts during the decoking process.

In order to reduce the quantity of coke formed, dilution steam may be added to the feedstock. For example, in one prior process, a hydrocarbon feedstock enters a pyrolysis furnace through one or more coils in a convection section of the furnace. Dilution steam is added to each coil such that a constant steam-to-feed ratio is maintained, typically in the range of 0.3 to 0.6 pounds of steam per pound of hydrocarbon feed. The steam/feed mix may be further heated in the convection section of the furnace before entering the radiant section, where the steam/feed mix is heated to the temperature required for cracking and conversion of the hydrocarbons to olefins. The dilution steam in the mixture reduces coke formation in the tubes. The effluent from the coils is then quenched and the raw product is sent for storage or processing.

Even with the use of dilution steam, coke formation is a problem. In some processes, adiabatic reactors have been used downstream of a pyrolysis furnace to allow improved conversion of hydrocarbons to olefins, while reducing fouling of the coils in the radiant zone. In these processes, a pyrolysis furnace of the type described above is used, and the reaction conditions, in particular temperature and flow rate, are controlled to reduce the conversion of the hydrocarbon to olefins within the coils in the furnace. The reduced conversion within the coils results in reduced coke formation. A downstream adiabatic reactor is used to further convert the feedstock to olefins, thereby improving the overall conversion. Even in these processes, coke formation requires periodic down time for decoking.

In the processes described above, heavier hydrocarbons such as naptha are used as the feedstock. The use of lighter hydrocarbons such as methane or natural gas as a feedstock to produce olefins has been limited because conversion of methane requires an initiator or relatively high temperatures (greater than 1100° C.). The temperatures required are greater than those typically obtained in a pyrolysis furnace. For example, the Benson process to produce olefins from methane uses chlorine as a free radical initiator at high temperatures. This process creates very corrosive conditions, and is therefore expensive and difficult to operate.

Another process used to convert methane to olefins is oxidative coupling of methane. In this process, the methane is partially burned, and a suitable catalyst is required to promote the conversion reaction.

Because methane and natural gas are abundant and relative inexpensive compared to other hydrocarbons, it would be desirable to have an improved process for conversion of methane and natural gas to olefins. It would also be desirable to have a process for cracking naptha or other hydrocarbons that resulted in reduced down time of the reactor or pyrolysis furnace for decoking.

SUMMARY OF THE INVENTION

The present invention is directed to improved processes for production of olefins from a hydrocarbon feedstock. In one embodiment of the process, a pyrolysis furnace having a plurality of coils is used to crack a hydrocarbon feedstock. During a first period of operation, one or more of the plurality of coils carries a mixture of the hydrocarbon feedstock and dilution steam, and the remainder of the plurality of coils carry only steam. Within the pyrolysis furnace, the contents of the coils are heated. In the one or more coils carrying a mixture of hydrocarbons and steam, the hydrocarbons are heated to a temperature sufficient to obtain partial conversion of the hydrocarbons to olefins. The temperature and residence time are controlled to obtain a desired level of conversion of the hydrocarbons In the coils carrying only steam, the steam in the coils is superheated. The coil effluents are combined and sent to an adiabatic reactor for further conversion of the feedstock to olefin product. Combining the coil effluents results in fluid-fluid heat transfer, and the energy required to convert the hydrocarbon feedstock to olefins in the adiabatic reactor is provided from the superheated steam. The product from the adiabatic reactor is fed to a quenching unit to reduce the temperature of the gases and stop the conversion reaction. The product stream from the quenching unit may be sent for storage or further processing.

Because steam alone can be used to decoke fouled radiant coils, after a selected time the flow through the tubes can be switched and the pyrolysis furnace operated for a second period. During the second period of operation, steam only flows through the coils that had previously included hydrocarbon feed. Coke deposited in these coils during the first period of operation will be reduced or eliminated because the steam temperature is high and the duration of the operation is long. At the end of the second period of operation, the flow through the coils can be again switched to provide decoking of the coils that were used for hydrocarbon cracking during the second period of operation. The material flow can be alternated in this manner as required to obtain the desired conversion of hydrocarbons to olefins. By sequentially alternating the material carried in the coils, on-line decoking of the coils occurs, which results in longer run times between shut downs for off line decoking.

The pyrolysis furnace may be designed to have a convection zone for preheating the hydrocarbon feedstock and a radiant zone where the hydrocarbon feedstock is heated to the temperature required for conversion to olefins. In other embodiments, heat may be recovered from the quenching unit to generate at least some of the dilution steam required for the process.

In another embodiment of the process, methane or natural gas is converted to olefins. In this embodiment, a reactor is provided that is insulated on the interior using a ceramic insulation material. The reactor may be a tube type reactor with an internal ceramic insulation.

Hydrogen and oxygen are introduced into a first stage of the reactor and combusted. Less than the stoichiometric quantity of oxygen is typically used. The combustion produces very high temperatures, typically 1200° C. or greater, in the first stage of the reactor. Hydrogen free radicals are also produced from excess hydrogen. Methane or natural gas is injected into a second stage in the reactor and dissociates to form $CH_3^-$ free radicals. A free radical reaction is initiated and produces hydrogen, acetylene, ethylene and small quantities of heavier hydrocarbons. The required heat for the reaction is provided by cooling the hot gases generated in the first stage of the reactor. The effluent from the reactor is sufficiently cooled to allow quenching in conventional equipment.

Among the advantages of the process is that longer run times and higher on-line factors improve the economics of the process. Higher yields of olefins as compared to other processes may also be obtained. In addition, in some embodiments, less expensive methane or natural gas may be used as a feedstock. Other advantages of the process will be apparent to those skilled in the art based upon the detailed description set forth below.

DETAILED DESCRIPTION OF THE INVENTION

In one embodiment of the process of the present invention, a hydrocarbon feedstock is cracked to form olefin products using a pyrolysis furnace and an adiabatic reactor. Generally, the pyrolysis furnace is comprised of a plurality of coils. A portion of the plurality of coils contains the hydrocarbon feedstock to be cracked, such as for example naptha, and dilution steam. The remaining portion of the plurality of coils contains only steam. As the hydrocarbon and steam stream pass through the pyrolysis furnace, the hydrocarbon feedstock is partially converted to olefins. In the coils containing only steam, the steam is superheated as it passes through the pyrolysis furnace.

The outlet from the coils is combined and fed to an adiabatic reactor, where additional conversion of the hydrocarbon feedstock takes place. As a result of fluid-fluid heat transfer in the combined stream, the heat in the superheated dilution steam will provide the necessary energy for additional conversion of the hydrocarbons in the adiabatic reactor.

The conversion of hydrocarbons to olefins in the coils generates various by-products, including coke on the inner surface of the coils. After a period of time, the material flows in the coils are switched, and the coils that were carrying the hydrocarbon feedstock and dilution steam will carry steam only, while the coils that had been carrying steam only will carry the hydrocarbon feedstock and dilution steam. By passing steam only through the coils that had previously carried the hydrocarbon feedstock and steam, coke deposited in the coil will be reduced or removed. This allows longer operation of the furnace between shut downs for decoking.

The outlet from the adiabatic reactor is fed to a quenching unit to cool the combined gas stream and terminate the hydrocarbon conversion reaction. The product stream from the quenching unit is sent for storage or further processing.

Descriptions of embodiments of this aspect of the invention are provided below. It will be understood that these descriptions are provided as examples and are not intended to limit the full scope of the invention as described herein or recited in the appended claims.

Figure 1:
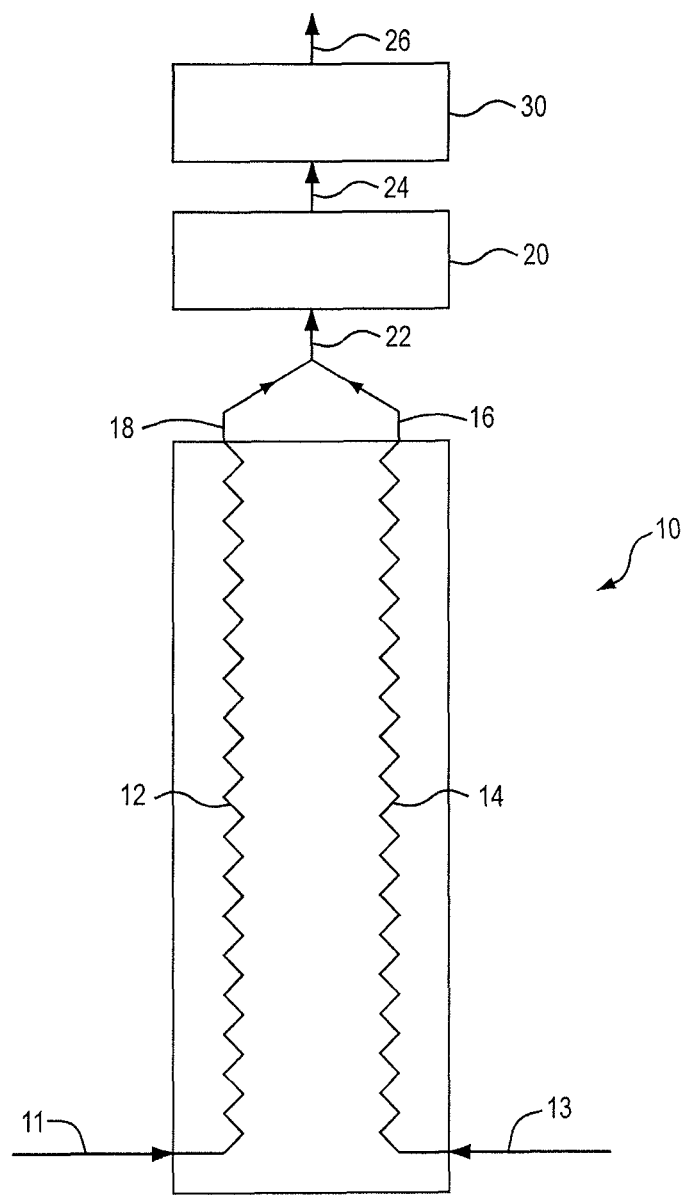
FIG. 1 is a schematic drawing of an embodiment of the process of the invention showing a two coil pyrolysis furnace.

A schematic of one embodiment of the process is shown in FIG. 1. In this schematic, a two coil furnace is shown. It will be understood by those skilled in the art that a furnace utilizing the process described below may contain any number of coils. In addition, in a furnace containing more than two coils, the coils may be arranged such that various flow configurations are used, such as for example two hydrocarbon feed/steam coils and one steam only coil, three hydrocarbon feed/steam coils and two steam only coils, etc. Those skilled in the art, using the information provided herein, can readily determine how to arrange the flow through the coils in the pyrolysis furnace to achieve the desired conversion of the hydrocarbon feedstock.

Referring to FIG. 1, a pyrolysis furnace (10) having two coils (12), (14) is shown. During a first period of operation, coil (12) is fed through line (11) a mixture of the hydrocarbon feedstock to be cracked and dilution steam. The proportion of dilution steam to hydrocarbon feedstock is typically in the range of 0.1 to 1.0 by weight. If desired, the hydrocarbon feedstock may be fed to the pyrolysis furnace without dilution steam. The hydrocarbon feedstock to coil (12) may be preheated before or after the addition of dilution steam. As described below, in some embodiments, the pyrolysis furnace may include a convection section to provide preheating to the hydrocarbon feedstock before it is combined with steam. The hydrocarbon feedstock is typically fed to the pyrolysis reactor at a temperature of from 250° C. to 750° C.

During the first period of operation, coil (14) is fed steam only through line (13). The steam is typically fed at a temperature from 150° C. to 800° C. The coils pass through the pyrolysis furnace, where the contents of each coil are heated by burners in inside walls of the pyrolysis furnace.

As the hydrocarbon feedstock in coil (12) pass through furnace (10), the hydrocarbon feedstock is heated to a temperature sufficient for conversion of a portion of the hydrocarbon feedstock to olefins, typically to a temperature of from 700° C. to 800° C. The flow rate in the coils is maintained to achieve a residence time for the hydrocarbon feedstock in the furnace required to obtain the desired level of hydrocarbon conversion. Typically, the residence time in the furnace is from 100 milliseconds to 800 milliseconds. A portion of the hydrocarbons in coil (12) is converted to olefins. The degree of conversion is controlled by adjusting the temperature and residence time in the reactor. The conversion of hydrocarbons in the furnace is lower than in conventional pyrolysis furnaces used for hydrocarbon cracking, and may be in the range of about 50%. Because the hydrocarbon conversion is lower than in conventional furnaces, less coke is formed within the coils in the furnace.

As the steam in coil (14) passes through the furnace, the steam is superheated. Typically, the steam will be superheated to temperatures from 900° C. to 1100° C. at pressures from 10 psig to 200 psig. This steam is superheated because the specific heat of steam is low and there is no heat required for conversion of hydrocarbons in the coil. Because there is no hydrocarbon conversion taking place in coil (14) in this phase of operation, no coke is formed.

The coil outlets (18, 16) from the furnace (10) are combined in header (22) and fed to an adiabatic reactor (20). As a result of the hydrocarbon conversion in the pyrolysis reactor, the coil outlet temperature is typically from 750° C. to 1000° C. The adiabatic reactor may be a separate reactor vessel, or it may be an extension of the coils or the combined coil header (22) with enlarged diameter. Because the adiabatic reactor is not exposed to the hot flue gases in the pyrolysis furnace, the reactor may be insulated to minimize heat losses to the environment. Also, less expensive materials may be used for the adiabatic reactor. The inlets and outlets are preferably designed to promote rapid mixing of hydrocarbons and steam with minimum pressure drop and to minimize or eliminate dead zones in the reactor. The design should minimize coke formation in the adiabatic reactor.

The volume of the reactor, and the length to diameter ratio for tubular reactors, is chosen to provide an adequate residence time for the desired conversion of the hydrocarbon feed to take place. Multiple adiabatic reactors may be used. Each adiabatic reactor may be directly connected to a quenching unit. In one embodiment, the quenching unit is a transferline exchanger, and the adiabatic reactor is incorporated in the transferline exchanger design. Transferline exchangers are typically designed to minimize the inlet residence time. By designing the transferline exchanger to increase the inlet residence time to allow further conversion of hydrocarbons, the inlet section of the transferline exchanger can function as an adiabatic reactor. This can minimize the total cost of the system or eliminate the need for a separate adiabatic reactor.

Where multiple coils are used in a furnace, two or more coils may be fed to a single adiabatic reactor. A single coil may also be fed to multiple adiabatic reactors, such as multiple adiabatic reactors integral with a transferline exchanger as described above. The quenching unit may also be a conventional shell and tube heat exchanger, a double pipe or linear exchanger, or a quick quencher.

In the adiabatic reactor, the superheated steam provides energy for further conversion of the hydrocarbons to olefins. The combined gases are cooled during the conversion process in the adiabatic reactor, typically to a temperature from 950° C. to 700° C. Overall conversion rates of 70% or more may be achieved.

The reaction product (24) is fed from the adiabatic reactor to a quenching unit (30). Because the gases are cooled in the adiabatic reactor, any type of quenching unit known to those skilled in the art may be used. Cooling for the quenching unit may be provided by an outside cooling source or, as described below, heat may be recovered through the quenching process for use in generating steam required for the process. In one embodiment, a transfer line exchanger (TLE) type quenching unit may be used in the process. The quenched raw product (26) is sent from the quenching unit for storage or further processing.

After a selected period of time, the materials fed through coils (14) and (16) are switched for a second period of operation. Steam only is fed through first coil (12) and a mixture of hydrocarbons and steam is fed through second coil (14). The steam flow through coil (12) removes coke deposited in the coil during the first period of operation. This on-line decoking allows the system to be operated for longer periods of time between off-line decoking. The hydrocarbons in the second coil (14) are converted to olefins as described above and combined with the steam generated in first coil (12) in header (22). The temperature, flow rates and other conditions are maintained as described above during the second period of operation.

At the end of the second period of operation, the flow through the coils can be again switched to provide decoking of the coils that were used for hydrocarbon cracking during the second period of operation. The material flow can be alternated in this manner as required to obtain the desired conversion of hydrocarbons to olefins while maintaining reduced coke levels in the coils. By sequentially alternating the material carried in the coils, on-line decoking of the coils occurs, which results in longer run times between shut downs for off line decoking.

Figure 2:
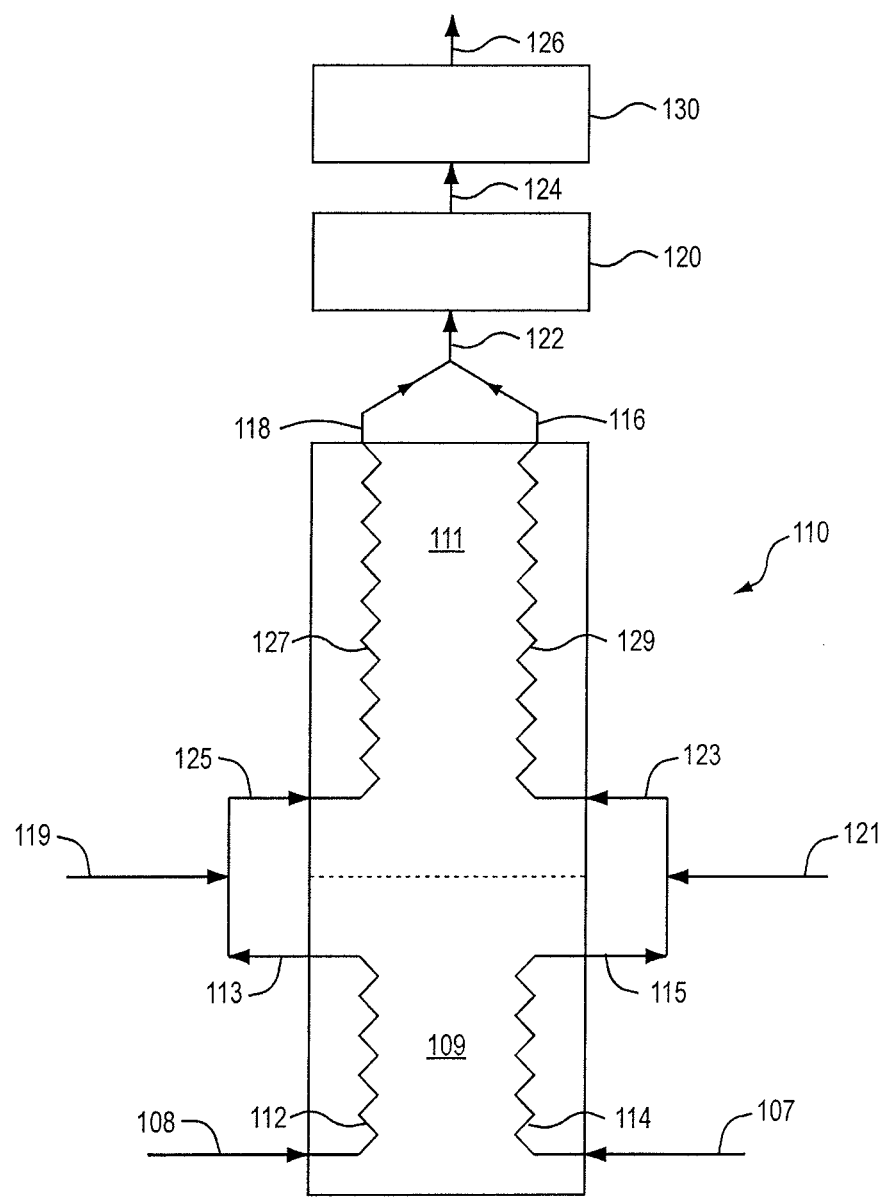
FIG. 2 is a schematic drawing of an embodiment of the invention in which the pyrolysis furnace has a convection zone and a radiant zone and dilution steam is injected to the hydrocarbon feed prior to entering the radiant zone.

Referring now to FIG. 2, a schematic of another embodiment of the process is shown in which the pyrolysis furnace (110) includes a convection section (109) and a radiant section (111). In a first period of operation, hydrocarbon feed (108) enters first coil (112) within convection section (109) of furnace (110) to be preheated. The hydrocarbon feedstock is typically fed to the pyrolysis reactor at a temperature of from 30° C. to 200° C. The convection section of the pyrolysis furnace is typically maintained at a temperature from 100° C. to 1200° C. After preheating, the hydrocarbon feedstock (113) is mixed with dilution steam (119) and the hydrocarbon/steam mixture (125) is fed to coil (125) within the radiant section (111) of the furnace. In the radiant section (111) the hydrocarbon/steam mixture is heated and the hydrocarbons are partially converted to olefins. The radiant section of the pyrolysis furnace is typically operated at temperatures from 1000° C. to 1300° C., and the hydrocarbon/steam mixture is heated to a temperature from 700° C. to 850° C. Residence time in the radiant section of the furnace is typically from 100 milliseconds to 800 milliseconds. In the embodiment shown in FIG. 2, dilution steam is added to the preheated hydrocarbon feedstock outside of the furnace. If desired, the steam addition line may inject the dilution steam to the coil inside the wall of the furnace.

In second coil (129), steam is fed through steam line (121) and passes through the radiant section (111) through coil (129). The steam enters at dilution steam temperature, and is superheated in the radiant section of the furnace. The steam is typically superheated to a temperature from 900° C. to 1100° C. at a pressure from 10 psig to 200 psig.

Alternatively, during the first period of operation, steam may be fed to coil (114) through line (107) and preheated in convection section (109). The steam will flow through lines (115) and (123) to coil (129) in the radiant section of the furnace. If desired, a portion of the steam can be fed through the convection section and additional steam can be added through line (121). The steam is superheated in the radiant section of the furnace as described above.

The coil outlets (118) and (116) are combined in header (122) and fed to adiabatic reactor (120). Coil outlet temperatures are typically from 750° C. to 1000° C. The adiabatic reactor may be of the types described above. In the adiabatic reactor, the superheated steam provides energy for further conversion of the hydrocarbons to olefins by fluid-fluid heat transfer. The combined gases are cooled during the conversion process. Overall conversion rates of 70% or more may be achieved. The reaction product (122) is fed (124) from the adiabatic reactor to a quenching unit (130). Because the gases are cooled in the adiabatic reactor, any type of quenching unit known to those skilled in the art may be used. For example, a transfer line exchanger (TLE) type quenching unit may be used in the process. The quenched raw product (126) is sent from the quenching unit for storage or further processing.

After a selected period of time, the materials fed through coils (127) and (129) are switched for a second period of operation. During the second period of operation, feed line (107) provides hydrocarbon feedstock to coil (114) within convection section (109) of furnace (110) to be preheated. After preheating, the hydrocarbon stream (115) is mixed with dilution steam (121) and the hydrocarbon/steam mixture (123) is fed to coil (129) within the radiant section (111) of the furnace. In the radiant section (111) the hydrocarbon/steam mixture is heated and the hydrocarbons are partially converted to olefins as described above.

In coil (127), steam is fed through steam line (119) and passes through the radiant section (111) through coil (127). The steam enters at dilution steam temperature, and is superheated in the radiant section of the furnace as described above.

Alternatively, during the second period of operation, steam may be fed to coil (112) through line (108) and heated in convection section (109). The steam will flow through lines (113) and (125) to coil (127) in the radiant section of the furnace. If desired, a portion of the steam can be fed through the convection section and additional steam can be added through line (119). The steam is superheated in the radiant section of the furnace as described above.

The steam flow through coil (129) in the radiant section (111) of the furnace removes coke deposited in coil (129) during the first period of operation. This on-line decoking allows the system to be operated for longer periods of time between off-line decoking. During the second period of operation, the hydrocarbons in coil (129) are converted to olefins as described above and combined with the superheated steam from coil (127) in header (122) and fed to adiabatic reactor (120) and quenching unit (130) as described above. The product stream (126) is sent for storage or further processing.

At the end of the second period of operation, the flow through the coils can be again switched to provide decoking of the coils that were used for hydrocarbon cracking during the second period of operation. The material flow can be alternated in this manner as required to obtain the desired conversion of hydrocarbons to olefins while maintaining reduced coke levels in the coils. By sequentially alternating the material carried in the coils, on-line decoking of the coils occurs, which results in longer run times between shut downs for off line decoking.

Figure 3:
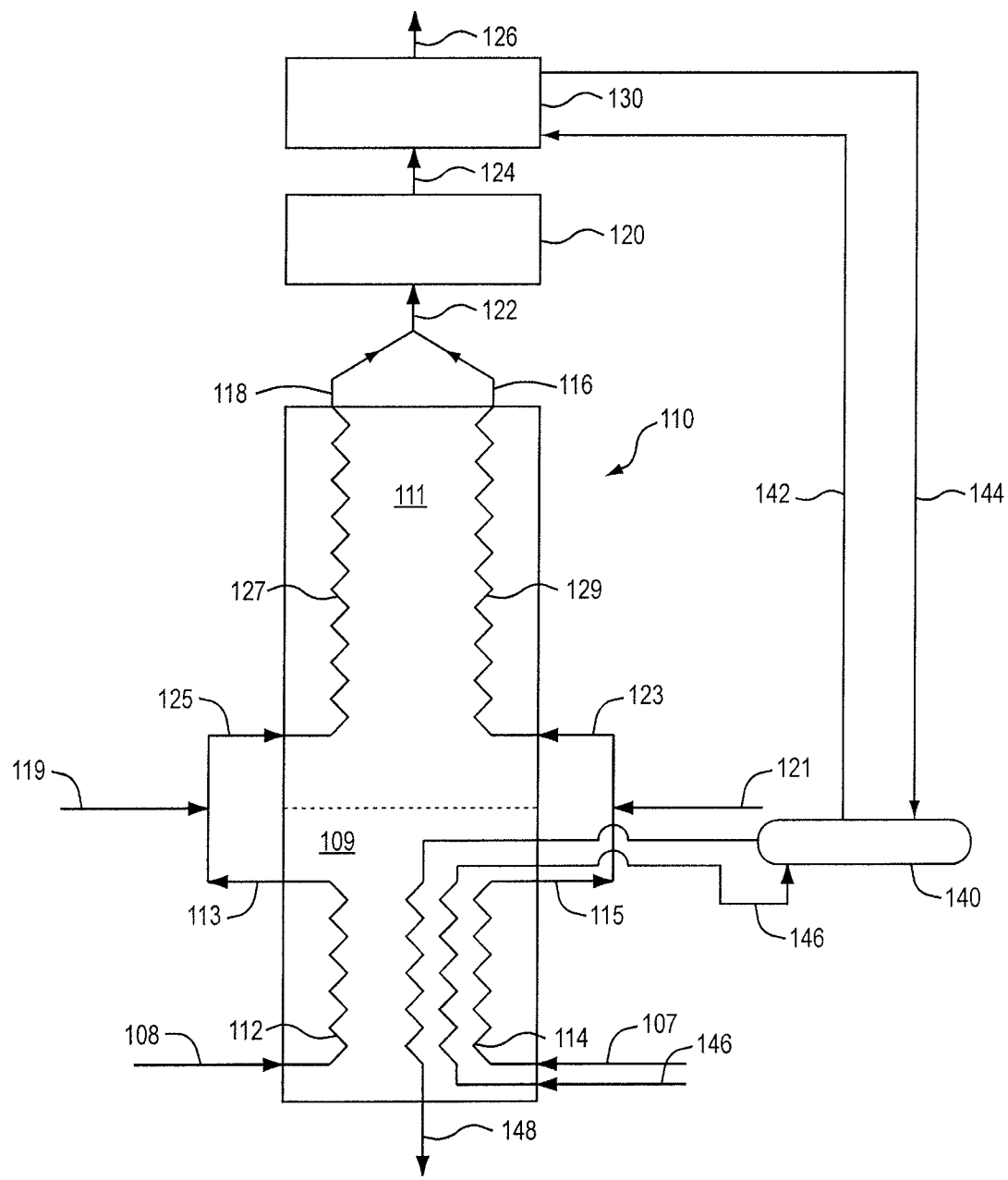
FIG. 3 is a schematic drawing of the pyrolysis furnace of FIG. 2 with a steam drum and associated lines for recovery of heat from a quenching unit.

In another embodiment of the process shown in FIG. 3, heat recovery in the quenching unit is used to provide steam for the process. Referring now to FIG. 3, in this embodiment, the pyrolysis furnace of FIG. 2 is used with a steam drum (140) added to the system. The pyrolysis furnace (110) and adiabatic reactor (120) are operated as described above to convert a hydrocarbon feed into olefin product. The steam drum (140) is connected to the quenching unit (130) by feed line (142) and steam return line (144). Water from the steam drum (140) is fed to the quenching unit (130) to provide at least part of the cooling duty for the product stream in the quenching unit. The water may be pumped from the steam drum to the quenching unit, or a thermosyphon system may be used.

Steam is generated in the quenching unit and fed back to the steam drum through line (144). The steam temperature is controlled as required to obtain the necessary cooling in the quenching unit. Typically, steam temperatures from the quenching unit will be from 160° C. to 330° C.

Feed water is provided to the steam drum (140) through feed line (146). The feed water may be preheated in the convection section of the pyrolysis furnace (110) as shown in FIG. 3. Alternatively, the feed water may be preheated in a separate heat exchanger or boiler. Steam generated in the steam drum may be further heated by feeding the steam through line (148) to the convection section (109) of the pyrolysis furnace (110). Alternatively, the steam may be further heated in a separate heat exchanger or boiler. By generating at least some of the dilution steam for the process in this manner, the process is more efficient and less input heat is required. High pressure steam at 250° C. to 330° C. may also be generated in this way and may be superheated in the pyrolysis furnace.

The following examples are prophetic and describe how one embodiment of the process may be performed in comparison to a prior process. Both examples describe the operation of two coils in a conventional pyrolysis furnace.

EXAMPLE I

The following example assumes two cracking coils, coil 1 and coil 2, in a conventional pyrolysis furnace. Under the prior processes of cracking to form olefins, each coil contains a stream comprising a mixture of 1000 Kg/h of naptha and 500 Kg/h of dilution steam. Feed conversion is 75% at a coil outlet temperature of about 850° C.

EXAMPLE 2

In this example, pyrolysis furnace with two cracking coils is assumed. Coil 1 carries 2000 Kg/h naptha and 400 Kg/h dilution steam. The naptha in this coil is cracked to about 50% conversion in the pyrolysis furnace by controlling the residence time in the furnace. By maintaining a shorter residence time, the coil outlet temperature will be about 850° C. In coil 2, approximately 1800 Kg/h of steam is carried. The steam in coil 2 is superheated in the furnace to about 1000° C. The naptha/steam mixture in coil 1 is mixed with the steam from coil 2 external to the furnace in an adiabatic environment. The energy in the superheated steam provides the energy required for further conversion of the hydrocarbons. Total conversion of 70% or more may be obtained.

After a period of time, the flow through the coils is switched. Coil 1 carries steam only and coil 2 carries the naptha/steam mixture. The steam flow in coil 1 removes some or all of the coke formed on the coil during prior operation.

Methane Conversion

In another embodiment of the process, a reactor is used to convert methane to olefins. Methane cannot be converted to olefins at conventional pyrolysis furnace temperatures. In this embodiment of the invention, hydrogen is combusted in a reactor with less than the stoichiometric amount of oxygen to produce a temperature in the reactor of 1200° C. or greater. The excess hydrogen forms hydrogen radicals that promote the methane conversion reaction. Methane is injected into the reactor, where it dissociates to form $CH_3^-$ free radicals. This initiates a free radical reaction resulting in formation of hydrogen, acetylene, ethylene and small quantities of heavier hydrocarbons and coke. The acetylene can be hydrogenated to produce additional ethylene.

Figure 4:
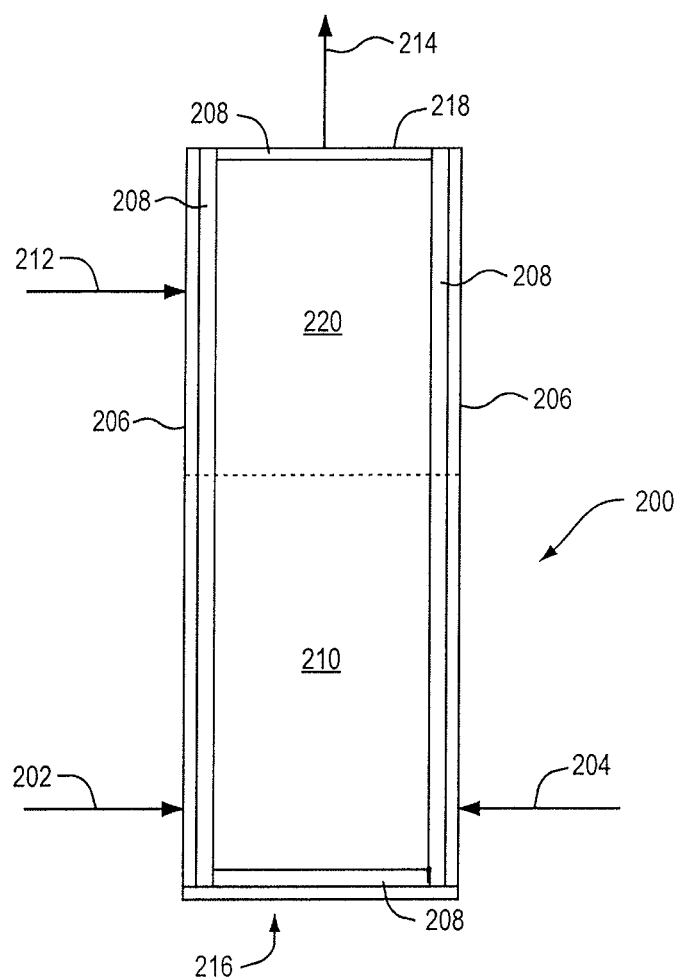
FIG. 4 is a schematic of an embodiment of the process wherein a reactor is used for cracking methane or natural gas to form olefins.

A schematic of a reactor for use in this embodiment of the invention is shown in FIG. 4. Reactor (200) comprises side walls (206), bottom wall (216) and top wall (218). The side walls, bottom wall and top wall may be comprised of any suitable material, and typically a metal such as steel will be used. Top wall (218) includes a product line (214) to remove the product stream from the reactor. Due to the high temperatures generated in the reactor, the side walls, the bottom wall and the top wall of the reactor include insulation layers (208). The insulation layer is typically a ceramic material. The ceramic materials used can include alumina, silicon carbides, silica-aluminas, carborundums or other conventional ceramic materials known to those skilled in the art. The ceramic insulation may include a catalyst material to further promote conversion of the methane to olefins.

It should be noted that the reactor is not limited to the configuration shown in FIG. 4 and described above. The reactor may be in any configuration, including a tube type reactor as described below.

Reactor (200) includes a first stage (210) and a second stage (220). In the first stage (210), hydrogen is fed through line (202) and combusted with less than the stoichiometric amount of oxygen fed through line (204). On a molar basis, the proportion of hydrogen to oxygen fed to the first stage of the reactor is from 2 to 10. The combustion of hydrogen and oxygen will produce a large amount of water in the form of steam. Some of the excess hydrogen may form hydrogen radicals which can promote the conversion of methane. Sufficient hydrogen and oxygen are combusted to raise the temperature of the gases in the first stage of the reactor to 1200° C. or greater. It should be noted that, if hydrogen is not available, methane may be used to raise the temperature in the first stage. If methane is used or other hydrocarbons are present in the first stage, CO and $CO_2$ will be produced, and water production will be slightly less.

Figure 5:
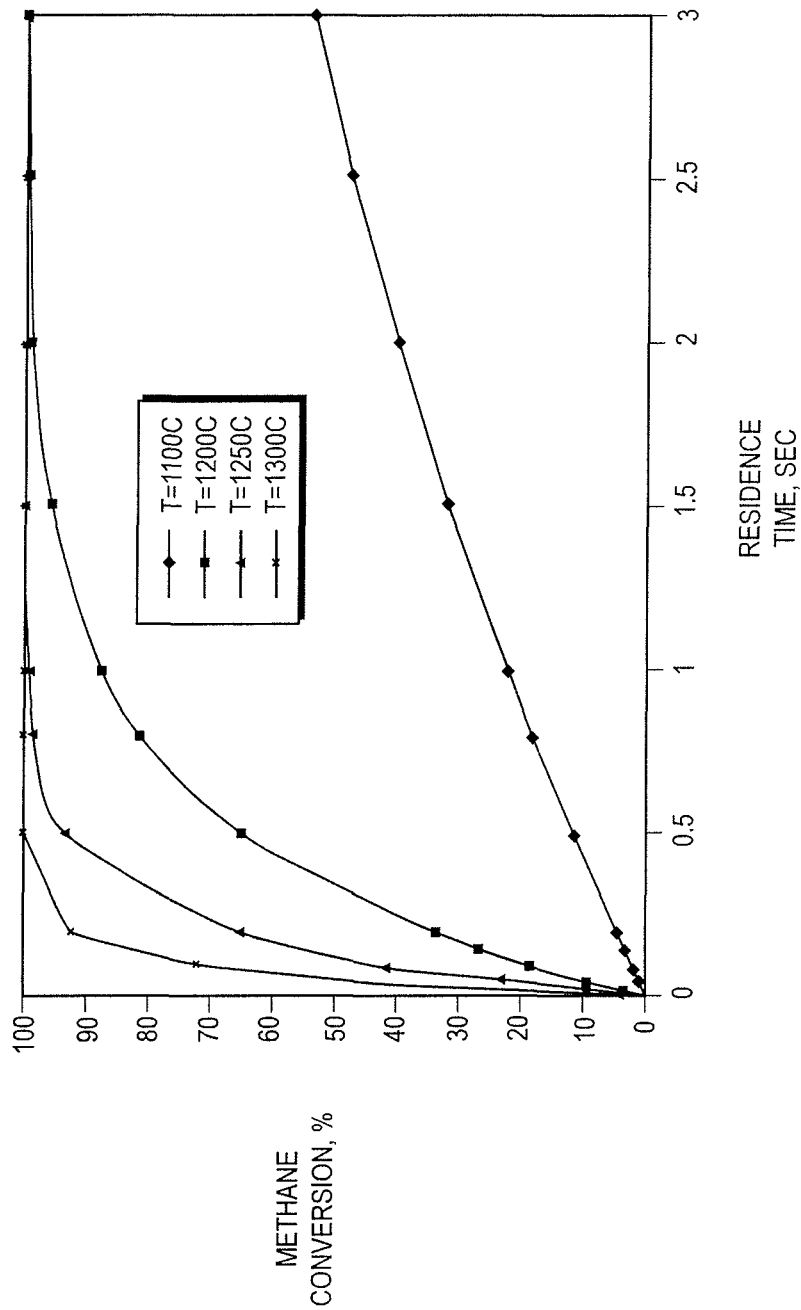
FIG. 5 is a chart showing the percentage of methane converted to olefins vs. residence time in the reactor at various reactor temperatures.

In the second stage (220) of the reactor, methane is injected into the heated gases through line (212). The methane dissociates to form $CH_3^-$ free radicals, initiating a free radical reaction and forming hydrogen, acetylene, and ethylene, and small quantities of heavier hydrocarbons and coke. As shown in FIG. 5, as temperature is increased, the yield of olefins from the methane increases and the residence time in the reactor can be shortened. At longer residence time, a large amount of carbon is produced. To obtain the desired olefin products, the residence time in the reactor is typically maintained under 0.5 seconds, and more preferably less than 0.2 seconds. At these residence times, the product may typically contain about 50% by weight ethylene and 45% by weight acetylene. Benzene (about 1% by weight) and other heavier hydrocarbons (remainder) are also produced.

The product gas is discharged from the reactor through product line (214) and sent for quenching. As the methane is converted to the olefin product, the required heat for the endothermic conversion reaction is provided from the hot gas formed in the first stage of the reactor. This cools the temperature of the gas such that, at the end of the second stage, the combined product gas can be quenched using conventional equipment, such as for example a transfer-line exchanger. Typically, the temperature of the product gas will be from 800° C. to 1100° C. Because the temperature is typically sufficiently reduced by the reactions in the second stage of the reactor, no special device or method is required for cooling the product gas stream.

Figure 6:
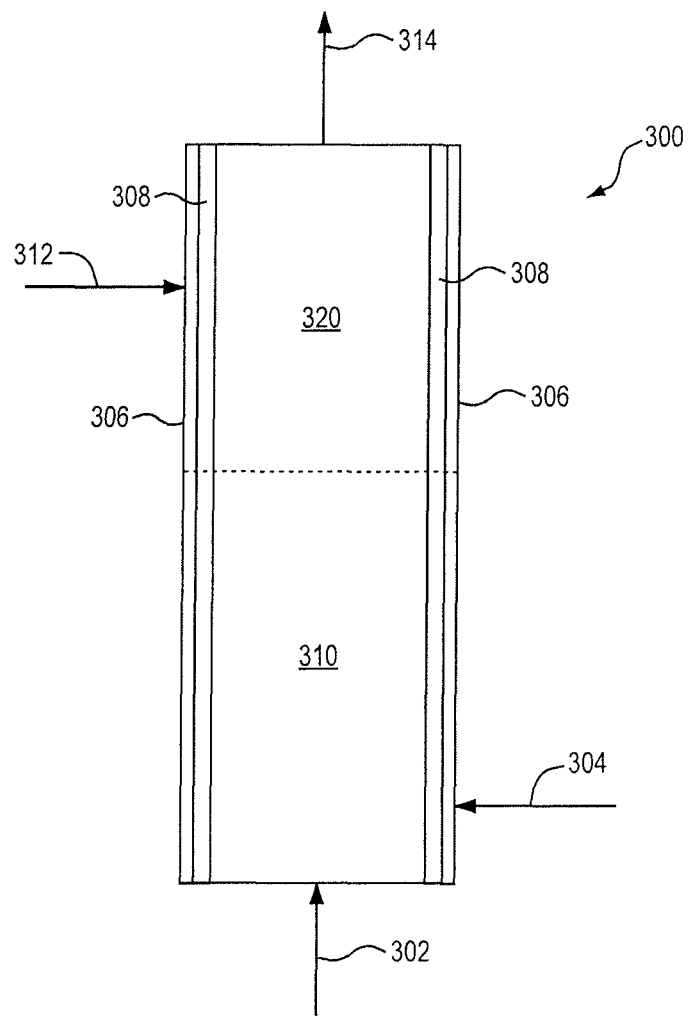
FIG. 6 is a schematic of a tube type reactor for cracking methane or natural gas to form olefins.

FIG. 6 shows a cross-sectional schematic of a tube type reactor for use in converting methane to olefins. The tube may be comprised of any appropriate material, and is typically a metal such as steel. The metal wall (306) has fixed to the inside diameter an insulation material (308). The insulation material is typically a ceramic of the type described above. Alternatively, the entire reactor tube may comprise a ceramic material. The insulation layer may include a catalyst as described above.

As shown in FIG. 6, reactor (300) includes a first section (310) and a second section (320). In the first section (310), hydrogen is fed into the tube (302) and less than the stoichiometric amount of oxygen is injected through line (304). It will be understood that, if desired, oxygen can be fed into the first section through the tube and hydrogen can be injected into the first section through line (304).

The hydrogen and oxygen combust in the first section. The combustion of hydrogen and oxygen will produce a large amount of water in the form of steam and free hydrogen radicals as described above. Sufficient hydrogen and oxygen are combusted to raise the temperature of the gases in the first stage of the reactor to 1200° C. or greater. As discussed above, if hydrogen is not available, methane may be used to raise the temperature in the first stage. If methane is used or other hydrocarbons are present in the first stage, CO and $CO_2$ will be produced, and water production will be slightly different.

In the second section (320) of the tube, methane is injected into the heated gases through line (312). The methane dissociates to form $CH_3^-$ free radicals, initiating a free radical reaction and forming hydrogen, acetylene, and ethylene, and small quantities of heavier hydrocarbons and coke. The residence time and temperature in the second stage of the reactor is controlled as described above to obtain the desired conversion of methane. The product gas is discharged from the reactor through the end of the tube (314) and sent for quenching. As described above, as the methane is converted to the olefin product, the required heat for the endothermic conversion reaction is provided from the hot gas formed in the first section of the tube. This cools the temperature of the gas such that, at the end of the second section, the combined product gas can be quenched using conventional equipment, such as for example a transfer-line exchanger. Therefore, no special device or method is required for cooling the product gas stream In all of the embodiments of the process described above, methane and/or naptha is described as the hydrocarbon feedstock. It will be understood by those skilled in the art that any hydrocarbon feed, including methane to processed or unprocessed gasoils can be used as feeds in the processes described and claimed. Any hydrocarbon feed can be used with an adiabatic reactor with high temperature steam providing the energy or hydrogen/methane combustion providing the energy.

To achieve a desired level of conversion for any type of feed, the endothermic heat duty must be satisfied. The minimum level of hydrogen required to satisfy the energy requirement should be fed to the reactor for combustion. A slight excess of hydrogen is acceptable, as the excess hydrogen will form hydrogen free radicals to initiate and promote the conversion reaction. If too much excess hydrogen is present, it can adversely affect the conversion of the hydrocarbon to olefins, as the olefins formed may be hydrogenated back to paraffins. Also, the compression power required to separate the products will increase and will adversely affect the economics. Therefore, the appropriate amount of hydrogen for the specific hydrocarbon feed should be fed to the reactor. By preheating the hydrocarbon feed without significant cracking, the amount of hydrogen required can be reduced.

While various embodiments of the have been shown and described, one skilled in the art will recognize that modifications may be made to the processes described above without departing from the spirit and scope of the invention. Accordingly, it is to be understood that the present invention has been described by way of example and not by limitation.

The invention claimed is:

1. A process for producing olefins from a hydrocarbon feed comprising the steps of:
   (a) providing a pyrolysis furnace having one or more first coils and one or more second coils;
   (b) feeding the hydrocarbon feed to the one or more first coils;
   (c) feeding steam alone to the one or more second coils;
   (d) heating the first and second coils in the pyrolysis furnace, wherein the temperature of the steam at the outlet of the second coils is in the range from about 900° C. to about 1100° C., the temperature at the outlet of the first coils is in the range from about 700° C. to about 800° C., and the residence time in the first coils is in the range from about 100 to about 800 milliseconds;
   (e) combining the outlet of the first and second coils to form a combined hydrocarbon/steam stream;
   (f) feeding the combined hydrocarbon/steam stream to an adiabatic reactor; and
   (g) quenching the outlet stream from the adiabatic reactor in a quenching unit.

2. The process of claim 1 further comprising the step of:
   (h) after a predetermined period of time, feeding steam through the one or more first coils and feeding hydrocarbon feed through the one or more second coils.

3. The process of claim 2, further comprising the step of adding dilution steam to the hydrocarbon feed as it is fed to the one or more first coils and the one or more second coils.

4. The process of claim 3, wherein the ratio of dilution steam to hydrocarbon feed is from 0.1 to 1.0 by weight.

5. The process of claim 2, wherein the number of first coils and the number of second coils is equal.

6. The process of claim 1, wherein the hydrocarbon feed is heated to a temperature of at least 750° C. in the pyrolysis furnace.

7. The process of claim 1, further comprising the steps of:
   (i) feeding the quenching unit with preheated water; and
   (j) generating steam in the quenching unit.

8. The process of claim 7, wherein the quenching unit is a transferline exchanger.

9. A process for producing olefins from a hydrocarbon feed comprising the steps of:
   (a) providing a pyrolysis furnace having one or more first coils and one or more second coils, wherein the pyrolysis furnace has a convection zone and a radiant zone;
   (b) feeding the hydrocarbon feed to the one or more first coils such that the hydrocarbon feed is preheated in the convection zone;
   (c) feeding steam alone to the one or more second coils;
   (d) heating the first and second coils in the pyrolysis furnace, wherein the temperature of the steam at the outlet of the second coils is in the range from about 900° C. to about 1100° C., the temperature at the outlet of the first coils is in the range from about 700° C. to about 800° C., and the residence time in the radiant zone is in the range from about 100 to about 800 milliseconds;
   (e) combining the outlet of the first and second coils to form a combined hydrocarbon/steam stream;
   (f) feeding the combined hydrocarbon/steam stream to an adiabatic reactor; and
   (g) quenching the outlet stream from the adiabatic reactor in a quenching unit.

10. The process of claim 9 further comprising the step of:
    (h) after a predetermined period of time, feeding steam through the one or more first coils and feeding hydrocarbon feed through the one or more second coils such that the hydrocarbon feed is preheated in the convection zone.

11. The process of claim 10, further comprising the step of adding dilution steam to the hydrocarbon feed as it is fed to the one or more first coils and the one or more second coils.

12. The process of claim 11, further comprising the steps of:
    (i) feeding the quenching unit with preheated water; and
    (j) generating steam in the quenching unit.

13. The process of claim 11, wherein the quenching unit is a transferline exchanger.

* * * * *